(12) United States Patent
Warren

(10) Patent No.: US 11,974,939 B2
(45) Date of Patent: May 7, 2024

(54) STRESS URINARY INCONTINENCE DEVICE

(71) Applicant: Remy—International Consumer Products Inc., Kitchener (CA)

(72) Inventor: Remy Warren, Kitchener (CA)

(73) Assignee: Remy—International Consumer Products Inc., Kitchener (CA)

( * ) Notice: Subject to any disclaimer, the term of this patent is extended or adjusted under 35 U.S.C. 154(b) by 73 days.

(21) Appl. No.: 17/810,702

(22) Filed: Jul. 5, 2022

(65) Prior Publication Data

US 2022/0401252 A1   Dec. 22, 2022

Related U.S. Application Data

(63) Continuation-in-part of application No. PCT/CA2021/050013, filed on Jan. 8, 2021.

(60) Provisional application No. 62/958,511, filed on Jan. 8, 2020.

(51) Int. Cl.
*A61F 5/455* (2006.01)
*A61F 2/00* (2006.01)
*A61F 5/44* (2006.01)

(52) U.S. Cl.
CPC .......... *A61F 5/4553* (2013.01); *A61F 2/0009* (2013.01); *A61F 5/4404* (2013.01)

(58) Field of Classification Search
CPC .... A61F 5/4553; A61F 2/0009; A61F 5/4404; A61F 2220/0008; A61F 2220/005; A61F 2240/004; A61F 2250/0015; A61F 2250/0019; A61F 2250/0036; A61F 2250/0059; A61F 2250/006; A61F 5/455
USPC ..................................................... 600/29–32
See application file for complete search history.

(56) References Cited

U.S. PATENT DOCUMENTS

| 5,074,855 A | * | 12/1991 | Rosenbluth ............... A61F 5/48 604/347 |
| 5,813,973 A | * | 9/1998 | Gloth ............... A61B 17/12099 600/29 |
| 5,895,349 A | * | 4/1999 | Tihon ..................... A61F 5/455 128/885 |
| 5,927,282 A | * | 7/1999 | Lenker ............. A61F 13/47209 128/885 |

(Continued)

FOREIGN PATENT DOCUMENTS

WO   WO1997028766 A1   8/1997

OTHER PUBLICATIONS

International Search Report dated Mar. 25, 2021—PCT/CA2021/050013.

(Continued)

*Primary Examiner* — Sunita Reddy
(74) *Attorney, Agent, or Firm* — Gowling WLG (Canada) LLP

(57) ABSTRACT

A stress urinary incontinence device is provided to limit or prevent leakage of urine in an individual. The device includes a body comprising an inner portion surrounded by an outer portion. The outer portion comprises biocompatible material and has a contact face opposing a guide face. The contact face is configured to occlude the urethral opening of the individual. A guide having an interior portion surrounded by an exterior portion projects from the guide face to aid in the application of the device onto the urethral meatus beneath the inner labia and above the vaginal opening of the individual. The device comprises materials that render it reusable.

19 Claims, 12 Drawing Sheets

(56) References Cited

U.S. PATENT DOCUMENTS

| | | |
|---|---|---|
| 9,408,684 B2 | 8/2016 | Berryman et al. |
| 9,555,151 B2 | 1/2017 | Taylor et al. |
| 9,795,705 B2 | 10/2017 | Berryman et al. |
| 10,010,393 B1 | 7/2018 | Nguyen et al. |
| 10,143,772 B2 | 12/2018 | Berryman et al. |
| 10,814,031 B2 | 10/2020 | Berryman et al. |
| 2005/0137557 A1 | 6/2005 | Swiecicki et al. |
| 2012/0165599 A1* | 6/2012 | Ellefson ............ A61F 13/34 600/29 |
| 2016/0095759 A1* | 4/2016 | Taylor ............... A61L 15/34 604/329 |
| 2016/0339142 A1* | 11/2016 | St. Anne ........... A61L 24/04 |
| 2017/0312116 A1* | 11/2017 | Laniado ........... A61F 5/4553 |
| 2018/0228642 A1* | 8/2018 | Davis ............... A61F 5/455 |
| 2019/0328927 A1 | 10/2019 | Berryman et al. |

OTHER PUBLICATIONS

Brubaker et al.—"The External Urethral Barrier", vol. 93, No. 6, Jun. 1999, pp. 932-937.

Newman, Diane K et al.—"Nursing Research" Nov./Dec. 2004 vol. 53 No. 6—Supplement, p. S42-S48.

\* cited by examiner

STRESS URINARY INCONTINENCE DEVICE

FIELD OF INVENTION

The present invention relates to a stress urinary incontinence device, particularly, a stress urinary incontinence device for females.

BACKGROUND OF THE INVENTION

Stress urinary incontinence, or loss of bladder control, is experienced during physical strain or exertion that increases abdominal pressure on the bladder. Urinary incontinence can be experienced at unexpected times of increased pressure on the bladder such as coughing, sneezing, laughing, standing, getting out of a car, exercising or heavy lifting. As a result, women experiencing such stress urinary incontinence may have to deal with personal distress, embarrassment, rashes or skin irritation, and perhaps disruption to social activities or relationships. To manage female mild to moderate stress urinary incontinence, women rely on either absorbent products such as pads, incontinence diapers, or pantyliners and/or preventative devices such as pessary devices.

Absorbent incontinence products are often readily available over the counter at pharmacies and retail stores. However, absorbent incontinence products do not limit embarrassing leaks caused by incontinence; rather, they soak up the urine after the leak has already happened. Additionally, absorbent incontinence products are generally single-use disposable products that can become very expensive to the user and can place a heavy burden on the environment.

As an alternative, or in addition, women can also use pessary devices that reduce or prevent the unintended leakage of urine. These devices must often be prescribed by a medical doctor or practitioner for internal fitting and sizing. Therefore, these devices are not readily available to women at their local pharmacies or retail stores as an option for the prevention of incontinence. Further, depending on the device, these devices may require specialized cleaning or education regarding internal placement to ensure safe and proper use. While some devices may be cleaned weekly, others may have to be removed by a medical professional every few months for regular cleaning.

Some preventative devices include Poise® *Impressa*® Bladder Supports, a single-use, tampon-like, internal, product. Other preventative devices include a urethra occluding device designed for the prevention of stress urinary incontinence, called Finess®. These devices are generally known to be single-use and disposable. In addition to being environmentally unfriendly, a limitation of the existing disposable devices is the loss of the device in a toilet receptacle if accidentally dislodged or if dropped during application. For example, if the device is not removed prior to urination, the device is likely to become dislodged due to the pressure from the act of urinating and will inevitably fall into the toilet receptacle. Given the single use nature of the device, the device will be lost or otherwise rendered unusable.

Consequently, a need exists for a reliable incontinence device for limiting unintentional urine flow due to stress urinary incontinence that is reusable.

SUMMARY OF THE INVENTION

A female stress urinary incontinence device for limiting leakage of urine is provided. The device comprises a body having an inner portion surrounded by an outer portion. The outer portion has at least one layer of biocompatible material configured to occlude the urethral opening. The outer portion of the body has a contact face opposing a guide face, and the body is for removable placement beneath the inner labia and above the vaginal opening. A guide projects from the guide face of the body to aid in the application of the device on the urethra. The contact face has a surface configured to receive at least one adhesive layer for adhering the device to the urethral meatus and over the urethral opening, and the biocompatible material renders the device to be reusable at least once.

In one aspect of the invention, thus, a female stress urinary incontinence device to limit or prevent leakage of urine in an individual is provided. The device comprises:
  a body comprising an inner portion surrounded by an outer portion, wherein said outer portion comprises a biocompatible material,
  said outer portion of the body comprising a contact face opposing a guide face, wherein said contact face is configured to occlude the urethral opening of the individual; and
  a guide projecting from the guide face to aid in the application of the device onto the urethral meatus beneath the inner labia and above the vaginal opening, said guide having an interior portion surrounded by an exterior portion, wherein the device comprises materials that render it reusable.

In another aspect, a kit is provided comprising: a stress urinary incontinence device as above described; and an adhesive for application to the contact face of the device.

In a further aspect, a method of limiting or preventing urine leakage from the urethra of an individual is provided. The method comprises applying a stress urinary incontinence device as above described to the urethral meatus to occlude the urethral opening.

BRIEF DESCRIPTION OF THE DRAWINGS

These and other features of the invention will become more apparent from the following description in which reference is made to the appended drawings wherein.

DETAILED DESCRIPTION

Figure 1A:
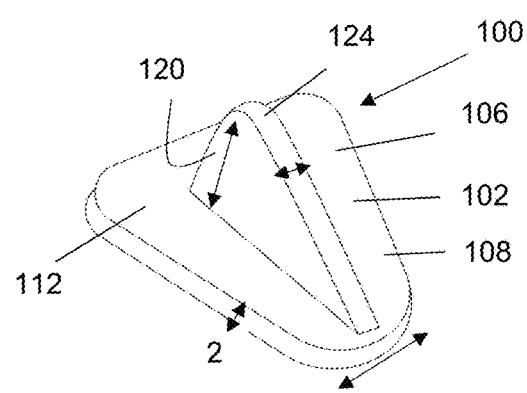
FIG. 1A shows a top perspective view of an exemplary stress urinary incontinence device in accordance with an embodiment of the present invention having generally a solid body.
Figure 1B:
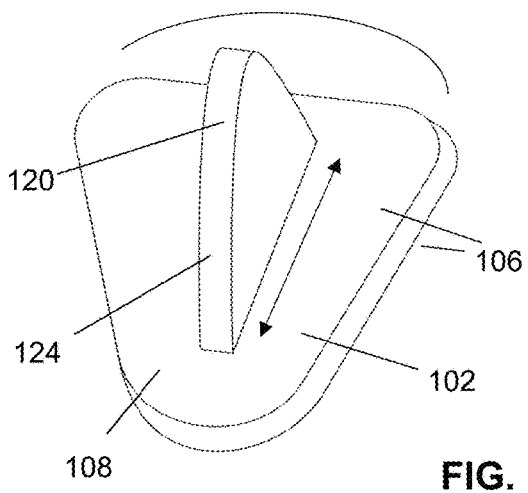
FIG. 1B shows an alternative top perspective view of the device of FIG. 1.
Figure 1C:
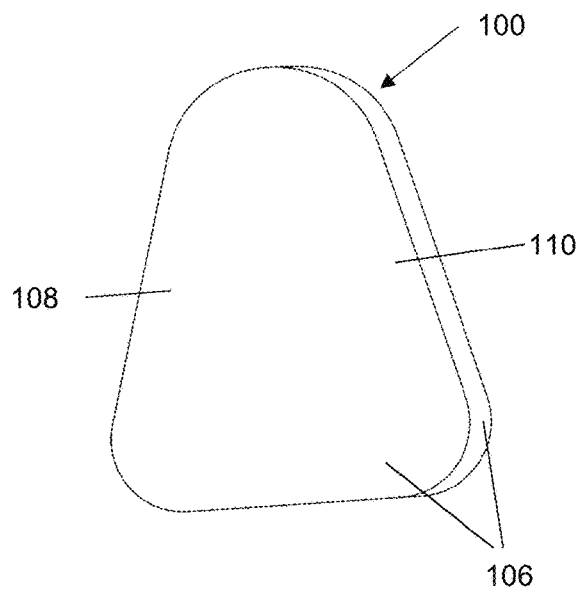
FIG. 1C shows a bottom plan view of the device of FIG. 1.
Figure 1D:
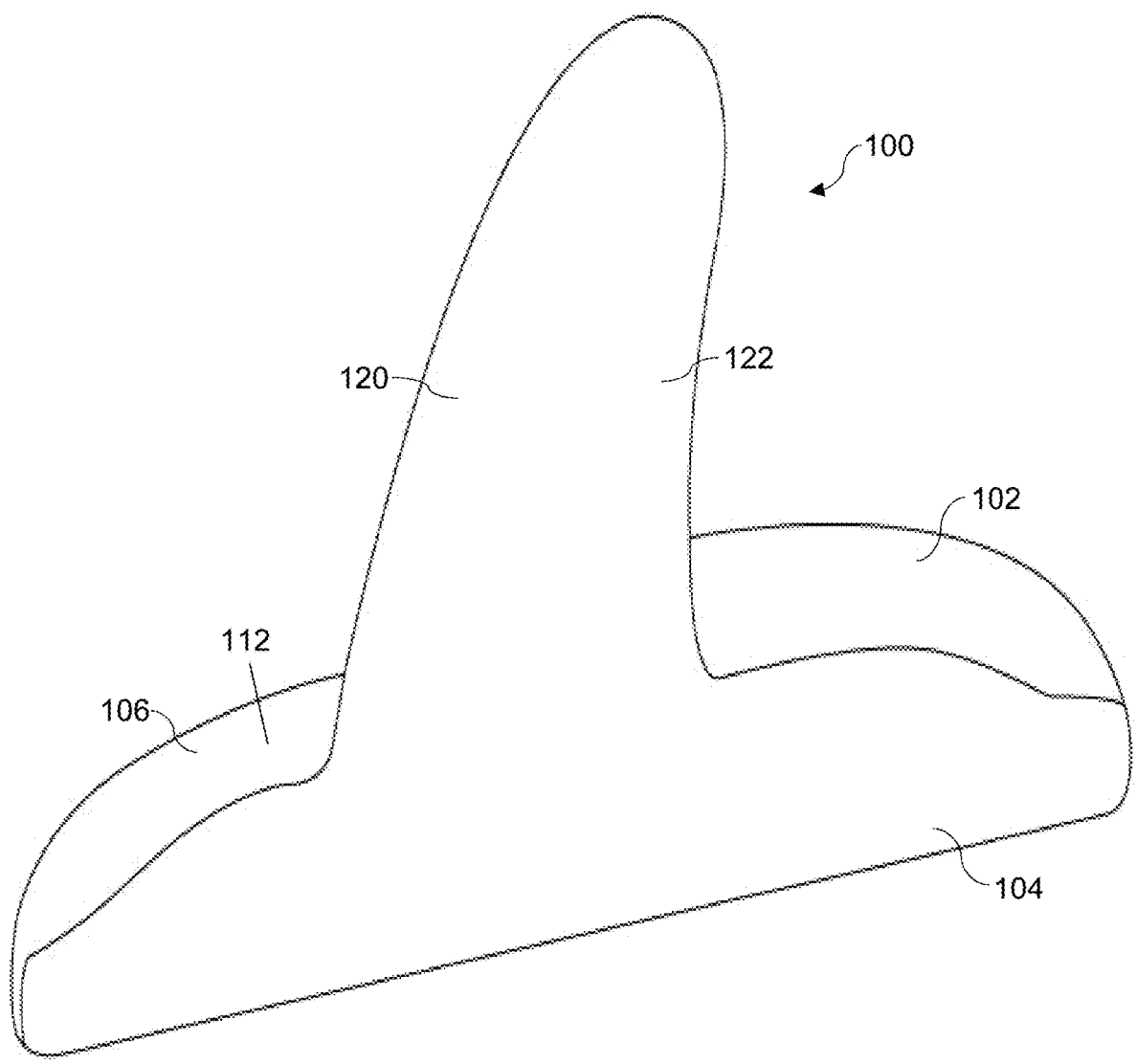
FIG. 1D shows a cutaway view of the device of FIG. 1.

The present disclosure provides a female stress urinary incontinence device for removable placement on the urethral meatus to occlude the urethral opening to limit or prevent leakage of urine and is placed beneath the inner labia and above the vaginal opening. Referring to FIGS. 1A-1D, a moulded incontinence device 100 is shown comprising a body 102 configured to occlude the urethral opening. The body 102 has an inner portion 104 surrounded by an outer portion 106. The outer portion 106 comprises biocompatible material 108. The body 102 has a contact face 110 opposing a guide face 112. A guide 120 projects from the guide face 112 of the body 102 to aid in the application of the device 100 on the urethra. The contact face 110 has a surface adapted to receive at least one adhesive layer 114 for adhering the device to the urethra. The contact face 110 of the device is designed to provide complete coverage of the external meatus over the urethral opening, above the vagina. Once placed, the guide sits on the urethral meatus over the urethral opening between the inner labia. The device is reusable at least once. The device is reusable, for example, based on the materials used in the device such that it maintains its integrity and functionality after use, and may additionally be washed and/or cleaned between uses.

Figure 7:
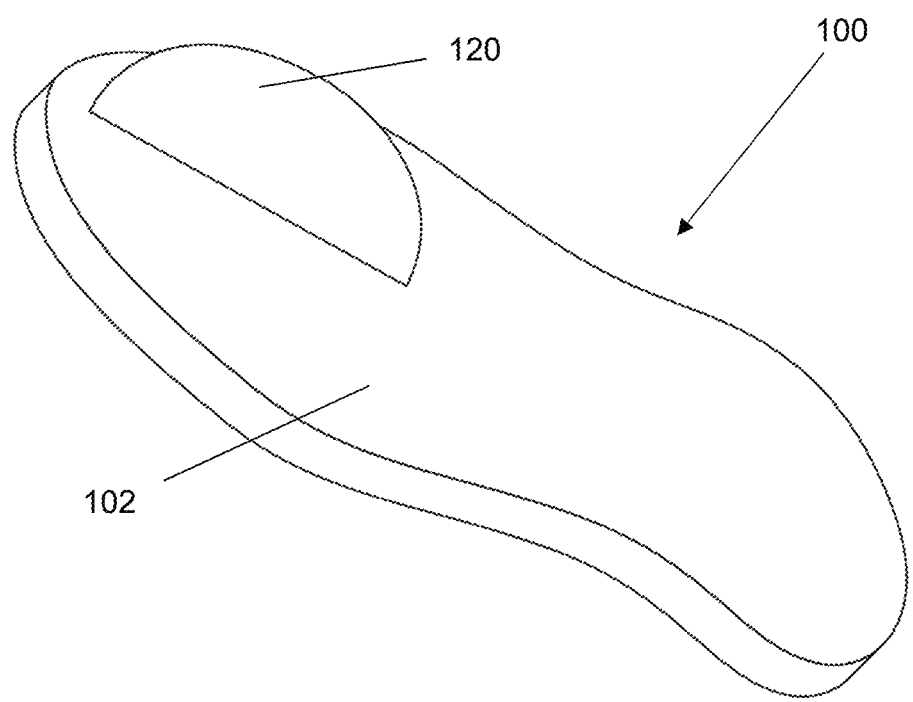
FIG. 7 shows an exemplary stress urinary incontinence device having a molded flat body with curvature in accordance with a further embodiment of the present invention.

In use, the device 100 when placed over the urethral opening can limit or prevent the unintentional leakage of urine from the urethra. Although generally shown as a triangular body in the accompanying drawings, the body 102 may assume other shapes, such as circular or oval, and may be rounded, curved, elongated (see, for example, FIG. 7), or any other suitable shape or modified shape, as will be known to one with skill in the art. A rounded or curved body may enhance user comfort during wear, minimizing harsh edges.

The body 102 may be a molded body of biocompatible material, such as a molded body of medical grade silicone, such that the entire body may be a solid molded body of medical grade silicone, i.e. the inner and outer portion 104/106 comprise the same material. Alternatively, the outer portion 106 of the body 102 comprises biocompatible material 108, while the inner portion 104 is made of a different material that may or may not be biocompatible. Suitable biocompatible materials that are reusable at least once are used, including, but not limited to, medical grade silicone (e.g. Elastosil®), silicone foam, medical grade foam, latex, PEEK (poly ether ketone), PE (polyethylene) plastic, PP (polypropylene thermoplastic), polyester, PPSF/PPSU (polyphenylsulfone), tetrafluoroethylene polymers such as polytetrafluoroethylene (Teflon®), polyamide elastomers such as Nylon® of varying polyamide content (e.g. nylon 12, nylon 6, nylon 66), polyamide block copolymers such as polyether block amide comprising carboxylic acid polyamide with an alcohol termination polyether, PEG (e.g. PeBax® and Vestamid®E) and latex rubber. The selected material may be used in natural form, or may be combined with a biocompatible color dispersion, such as Silcopas™, Stan-Tone™ or Silcotec™, to provide a colored device.

For ease of comfort, the body 102 of the device 100 may be comprised of varying shores (hardness) of material or be of different thicknesses throughout. For example, the body 102 of the device 100 may be thickest at the center of the device with decreasing thickness as it approaches the perimeter of the body 102 to enable greater comfort or flexibility during wear. In another example, the body 102 of the device 100 may be comprised of varying shores of silicone with a decreasing gradient of silicone towards the perimeter of the body 102 to enhance user comfort during wear. The varying degrees of thickness and/or decreasing gradient may provide greater flexibility to limit stiffness during wear and enable movement and a better fit for the user. For example, the body 102 of the device 100 may have a central shore (hardness) level of 20-30 on the durometer scale decreasing gradually to a shore (hardness) level of 10 towards the perimeter of the body 102 to provide enhanced comfort to the user during use.

Additionally, the device 100 may be of various sizes to fit different-sized individuals, i.e. sized for comfort to the user. For example, the body of the device at the contact face may be lengthened to cover the vaginal opening or may include a vaginal insertion feature for further bladder support. The adhesive thickness and the guide may also be modified without significant change to the function of the overall device.

In order to place the device, guide 120 may be used to help maneuver the device. The guide 120 comprises an interior portion 122 and an exterior portion 124, which may be the same or different. The guide 120 projects from the guide face 112 of the body 102 to aid in the application of the device 100 on the urethra. The guide 120 may be shaped as a triangular fin as shown in the accompanying drawings for ease of grasping the device 100 and guiding it for placement over the urethral opening. Alternatively, the guide 120 may be shaped as a rounded fin as shown, for example, in FIG. 7, for ease of grasping the device 100 and guiding it for placement over the urethral opening. Although not shown, the guide may comprise an opening such as in a ring, a knob or other suitable shape or feature as will be known to one with skill in the art to permit grasping and guiding of the device for placement. Furthermore, the guide and body may be integral; alternatively, the guide may be detachable from the body to permit removal of the guide once appropriately positioned, thereby enhancing comfort to the user during wear.

Figure 8:
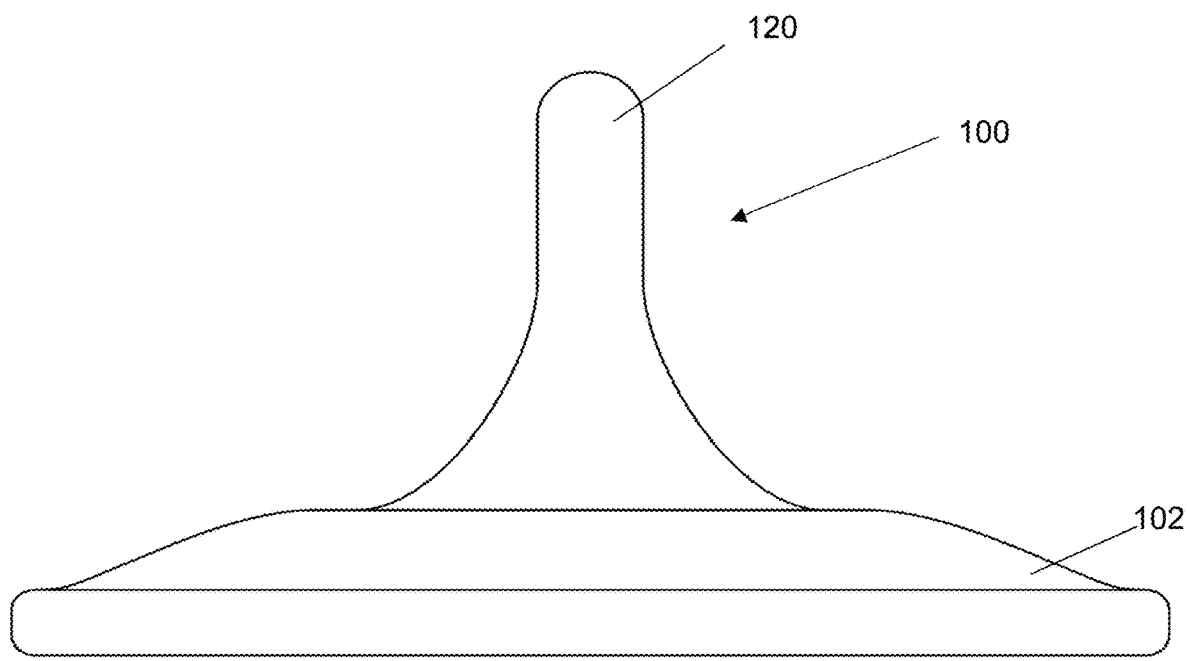
FIG. 8 shows an exemplary stress urinary incontinence device having a sloped guide in accordance with a further embodiment of the present invention.

Additionally, the guide 120 may comprise different thicknesses along its length, for example, the guide may be thicker at its base (which is connected to the body 102) and extend to a narrower thickness along its length rather than projecting directly from the body 102 at a single thickness (see, for example, FIG. 8). For example, the guide face 112 may have an angled slope/pitch leading up towards the guide 120, such a slope/pitch of <45 degrees, <30 degrees, <20 degrees, or <15 degrees.

In one example, the contact face 110 of the device is sized to comfortably sit on top of the urethral meatus. Thus, the guide 120 may be provided in varying sizes and shapes to fit different-sized individuals to maintain efficacy. If the body 102 of the device 100 is too large for a given individual, it will likely cause discomfort to the user and decreased efficacy as it would not properly sit on top of the urethral meatus. Similarly, if the body 102 of the device is too small to sit on the urethral meatus and cover the urethral opening, the primary function of the device, then the device would not efficiently prevent leakage. In one embodiment, the device is about 2.5-3.0 cm long, 1.8-2.5 cm wide at its base, and the guide is about 1.5-2.5 cm high.

In order to adhere the device 100 to the urethral meatus and over the urethral opening, the contact face 110 may be adapted to receive at least one biocompatible adhesive layer 114 that is non-toxic and biologically inert. The at least one layer of adhesive 114 may be pre-applied to the device 100 and the user may simply place the contact face 110 of the device 100 over the urethral opening for securement to the urethral meatus. Preferably, pre-applied adhesive is covered with a removable protective layer (or release liner) to preserve its adhesive property. The at least one layer of adhesive may be reusable at least once. It may, for example, be a medical grade, non-water gradient adhesive that is biocompatible. Exemplary adhesives include acrylate designed for medical/surgical use such as 3M' double coated medical tapes which can adhere to a wide variety of substrates, medical-grade hydrogels such as a silicone hydrogel, medical grade silicone, epoxies, epoxy-polyurethane blends, cyanoacrylates, and gel adhesive such as a slug-inspired medical adhesive or silicone-based adhesive with a self-tacking surface which may be washed/sanitized and further reused, such as Dupont™ MG 7-1020 or MG 7-9900 Soft Skin Adhesives.

Alternatively, the adhesive may be provided separately from the device, and applied onto the contact face 110 of the device by the user, with an applicator, brush or the like, prior to use. The adhesive, such as medical-grade non-water gradient adhesive, may also be provided as a separate adhesive strip (e.g. a double-sided adhesive strip). For hygienic purposes, a single-use adhesive may be preferred. Thus, the adhesive strip may be covered by a protective covering or liner (not shown) as would be known to one with skill in the art. The adhesive strip may be one that the user applies to the contact face 110 of the device 100. For example, the adhesive layer may be provided on an adhesive strip that is enclosed within a removable protective covering to prevent accidental adhesion to any surface with which the adhesive strip comes into contact. The user may then remove the protective covering or liner, and affix one side of the adhesive strip onto the contact face 110 of the device 100. Alternatively, an adhesive layer that is activated by wetting may be provided on an exposed or protected strip. Therefore, when wetted, the user may affix the wetted side of the adhesive strip onto the contact face 110 of the device 100. The opposite side of adhesive strip may then be applied, following wetting, if required to become adhesive, to the urethral meatus.

The adhesive may be selected to withstand variations in temperature and environmental conditions, e.g. to significantly maintain its level of adhesion over a range of temperatures and in the presence of small amounts of moisture. Further, the adhesive will preferably possess sufficient adhesive strength so that displacement of the device does not occur under normal movement, but it must not have such a strong adherence that it causes discomfort to the end user during removal. Additionally, the selected adhesive preferably exhibits minimal adhesion to body hair to further minimize discomfort on removal.

The double-sided adhesive strip may comprise different adhesives, for example, a first adhesive that adheres to the contact face of the device and a different second adhesive that adheres to the urethral meatus. These different adhesives may be layered (or laminated) directly onto one another, either manually or mechanically through an adhesive converting process. For example, the adhesive for the contact face of the device may comprise an acrylic and/or silicone adhesive such as but not limited to epoxies, epoxy-polyurethane blends, cyanoacrylates, or a silicone-based adhesive with a self-tacking surface, while the adhesive for application to the urethral meatus comprises a medical grade hydrogel such as medical grade silicone or silicone hydrogel, for example, Katecho's KM10 E Hydrogel in a 32 mil thickness or Axelgaard's AG2500 series medical grade hydrogels with a thickness of 50 mils.

For convenience, the double-sided adhesive strip may correspond in shape with that of the contact face. For example, for a device having a generally triangular contact face, the double-sided adhesive strip may similarly be cut into triangular shape. It may be die-cut or otherwise shaped as will be known to one skilled in the art. Where the double-sided strip is provided separately from the device, each side of the adhesive strip may be fitted with a release liner or protective covering as described above, such as PET (polyethylene terephthalate), LDPE (low-density polyethylene), PP (polypropylene) or a paper liner suitable for printing. Alternatively, or for further protection, the double-sided strip with or without a release liner, may be sealed in individual pouches, such as a polyfoil pouch, PET film pouch, mono-material PE pouch or other plastic film packaging, to maintain the stability of the combination and to limit exposure to contaminants.

Other suitable methods of applying at least one adhesive layer onto the contact face of the device are contemplated as will be known to one with skill in the art. Thus, in an aspect of the invention, a kit is provided comprising a device as described herein, and an adhesive for application to the contact face 110 of the body 102 as above described.

Figure 2A:
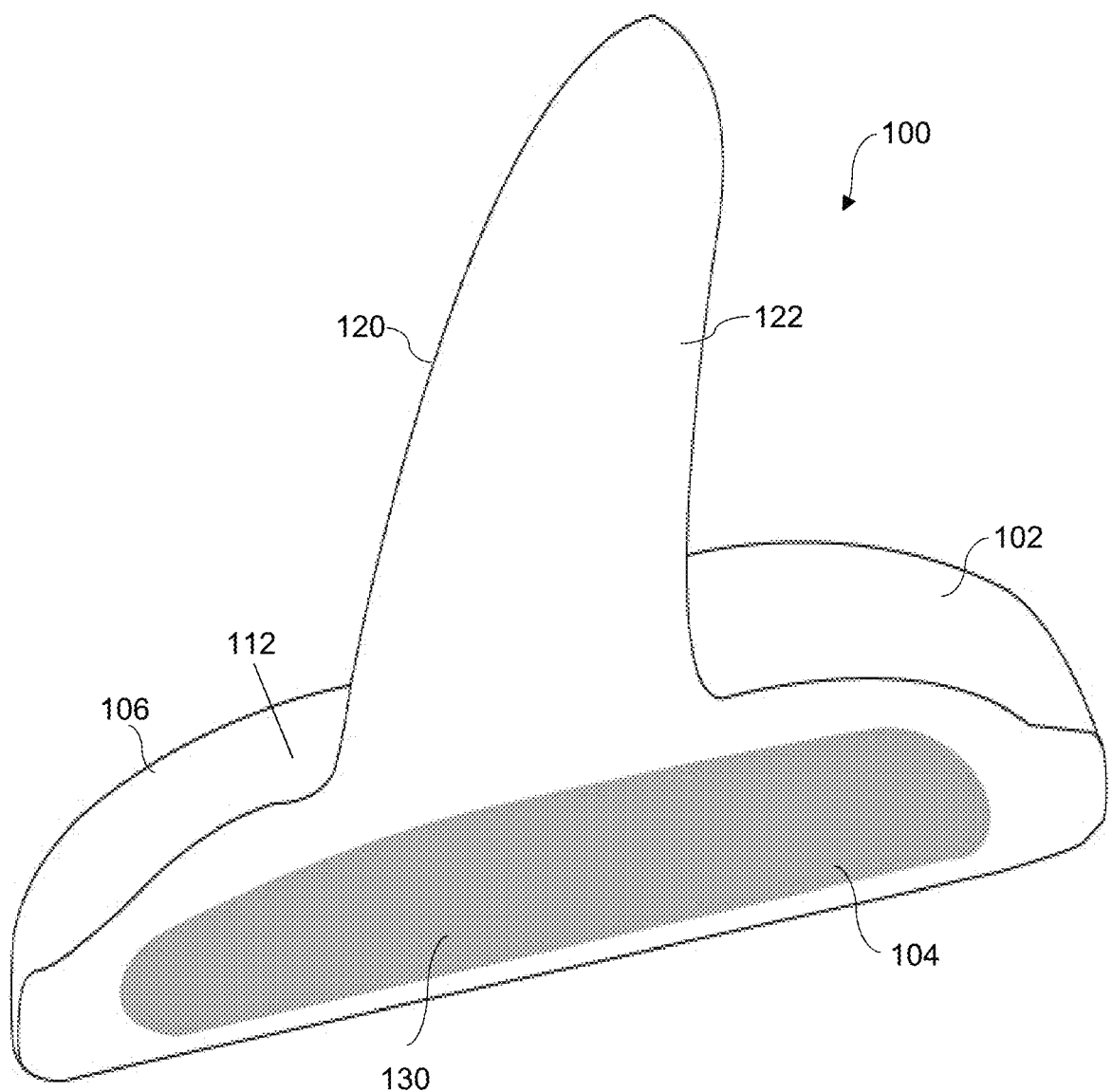
FIG. 2A shows a cutaway view of an exemplary stress urinary incontinence device having a foam interior layer in the body in accordance with a further embodiment of the present invention.
Figure 2B:
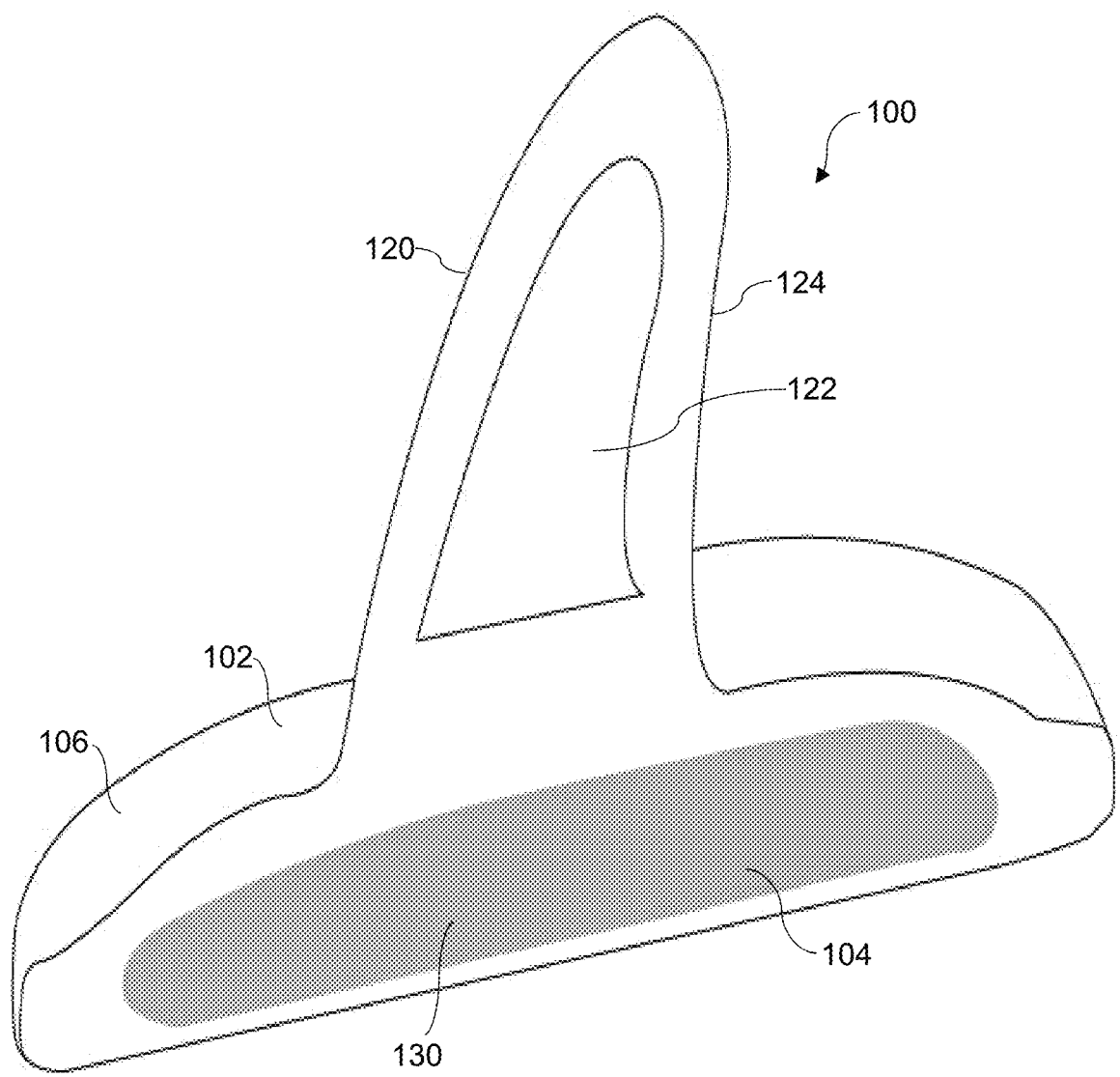
FIG. 2B shows a cutaway view of the device of FIG. 2A having an additional hollow interior in the guide in accordance with a further embodiment of the present invention.
Figure 3:
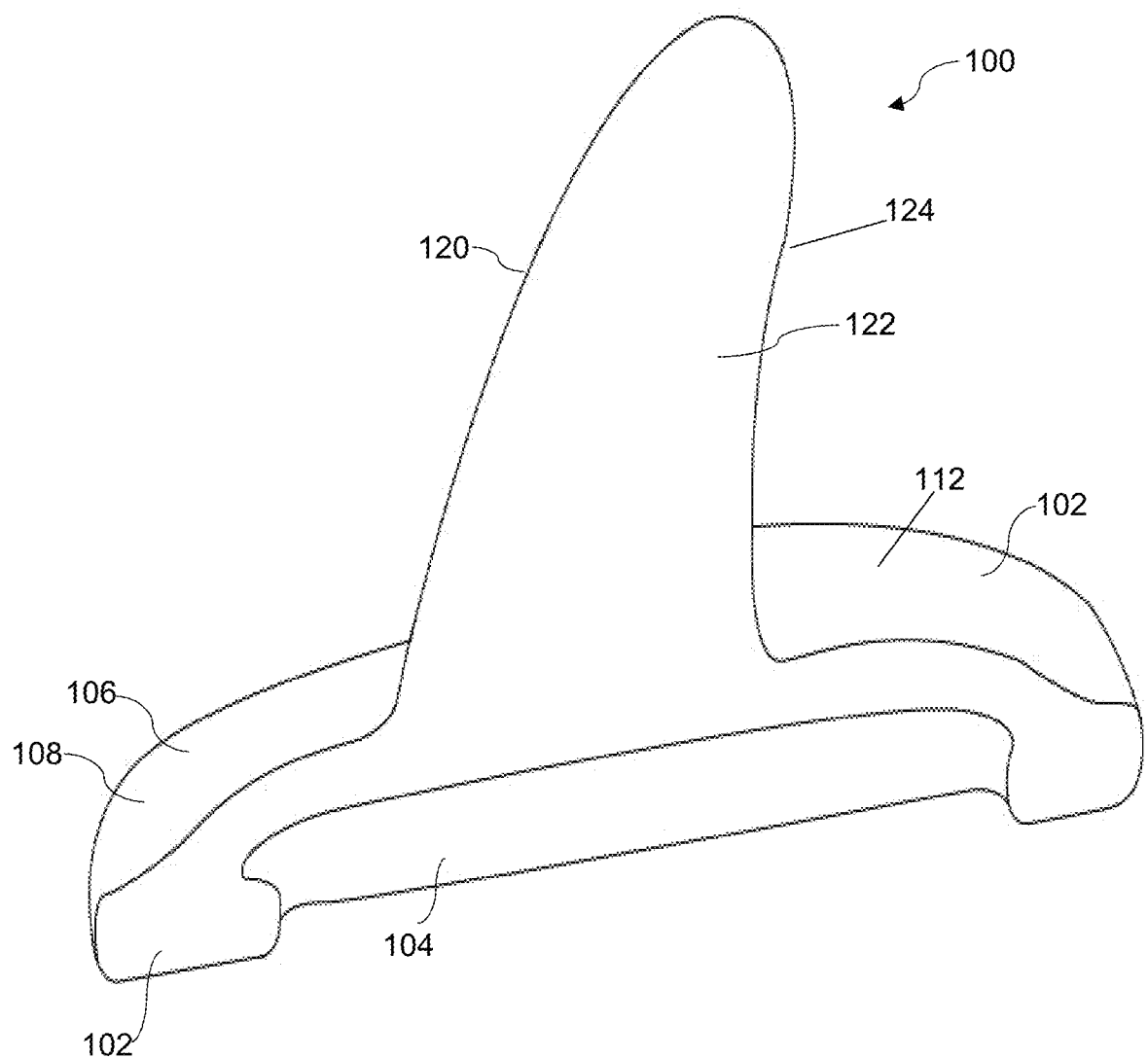
FIG. 3 shows a cutaway of an exemplary stress urinary incontinence device having a hollow inner portion in the body in accordance with a further embodiment of the present invention.
Figure 4A:
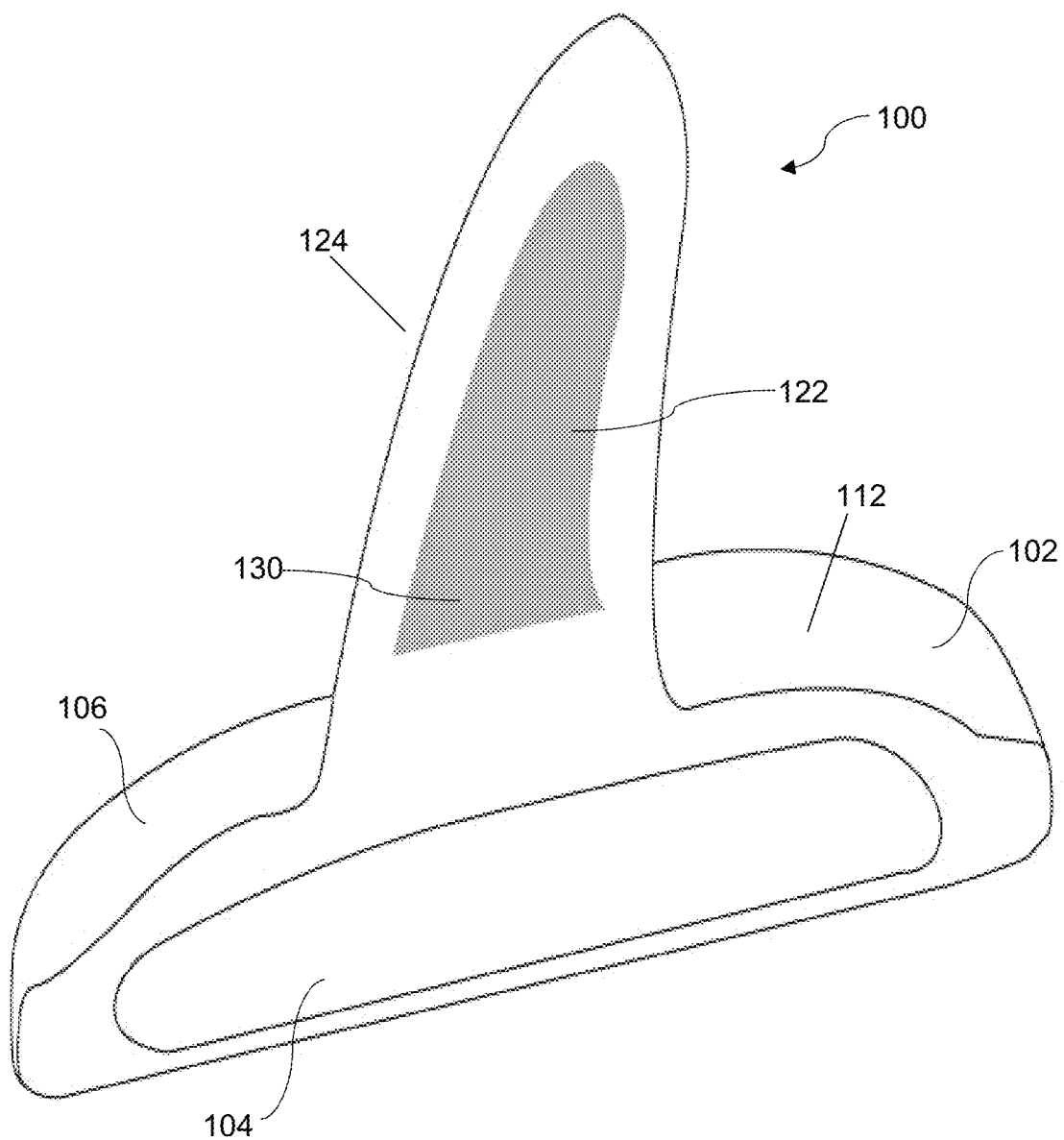
FIG. 4A shows a cutaway view of an exemplary stress urinary incontinence device having a foam interior in the guide in accordance with a further embodiment of the present invention.
Figure 4B:
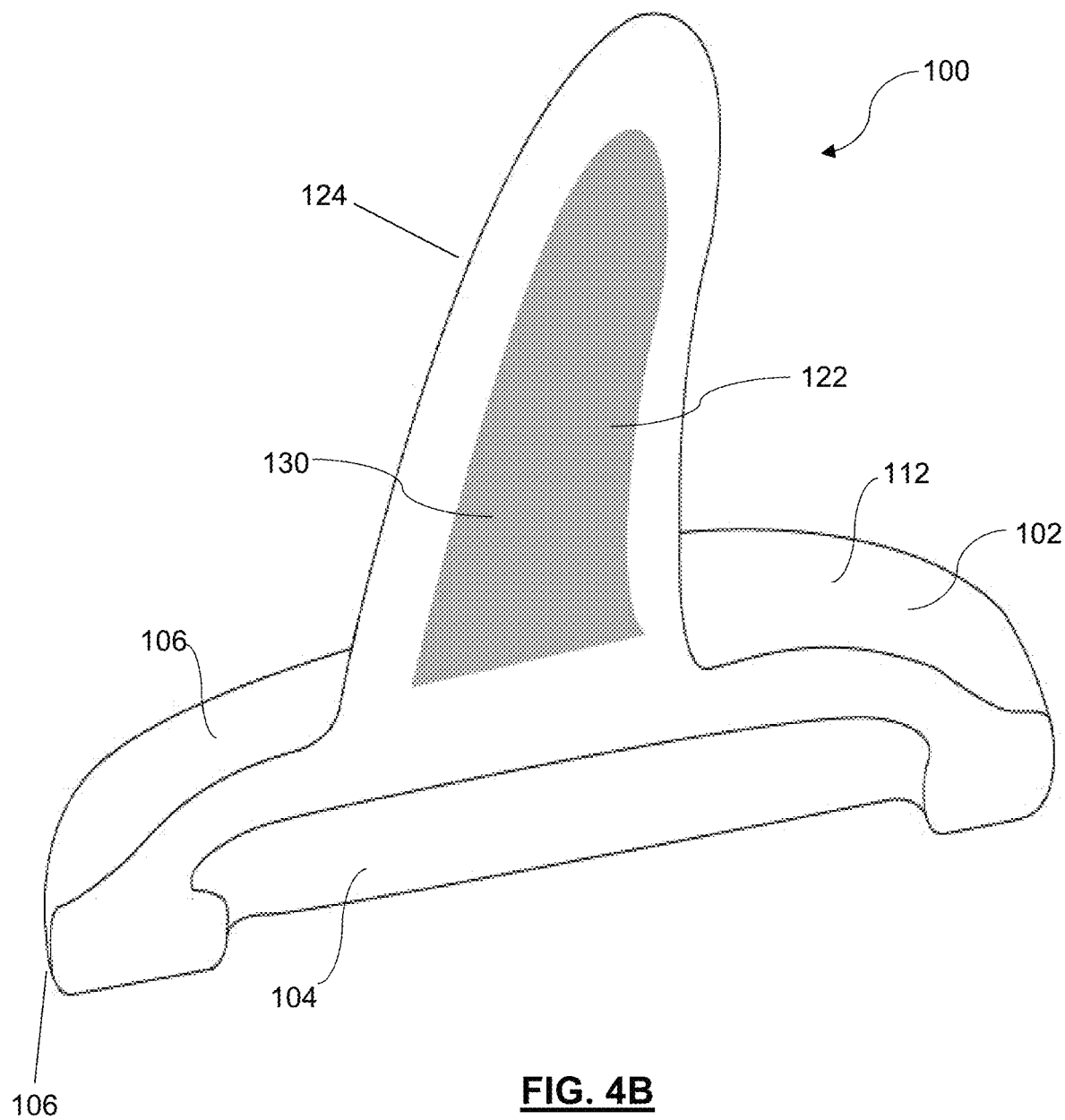
FIG. 4B shows a cutaway view of the device of FIG. 4A having an additional hollow interior in accordance with a further embodiment of the present invention.

As loss of the device is possible in liquid, such as in a toilet receptacle, the device may optionally be buoyant to enable ease of retrieval. This buoyancy may be enabled by the inner portion 104 of the body 102 being adapted to impart buoyancy on the device. Thus, the inner portion 104 of the body 102 may be at least partially hollow as shown in FIG. 2B, or may comprise at least one layer 130 of buoyant material such as silicone foam as shown, for example, in FIG. 2A. In another embodiment, the inner portion 104 of the body 102 may be partially hollow and include at least one layer of silicone foam. Therefore, the inner portion 104 of the body 102 may have a hollow portion and at least one layer of silicone foam; alternatively, the inner portion may have a hollow center encased by at least one layer of silicone foam. Alternatively still, the inner portion may have one layer of silicone foam that is spaced apart from the outer portion to provide a hollow area therebetween. In still other embodiments, the partially hollow inner portion may be webbed to provide several hollow chambers or bubbles to contribute to the buoyancy of the device. The webbing may be silicone foam or may be silicone of any suitable gradient. The webbing may also be any other material that is not necessarily biocompatible as it does not make direct contact with the user. Other materials that may be included in the inner portion to aid in the buoyancy of the device include, but are not limited to, PVC foam, styrofoam, and/or natural materials or biomaterials such as sponge, dolomite-containing biomaterial such as Gaia™, natural fibres such as moisture-resistant, quick-drying, resilient, and buoyant fibre including lignin, cellulose, carbohydrate or mixtures thereof such as Kapok, or mycelium mushroom filaments. Any suitable combination of these materials is also contemplated as will be known to one with skill in the art.

To contribute to the buoyancy of the device, interior portion 122 of the guide 120 may be partially hollow or filled with a buoyant material as described with respect to the body 102. Thus, the interior portion 122 of the guide 120 may comprise at least one layer of a buoyant material, such as silicone foam, to contribute to the buoyancy of the device. The guide 120 may have a hollow center encased by at least one layer of a buoyant material, may only have a hollow center, may only comprise a buoyant material, or may have a number of hollow spaces separated by webbing made of a buoyant material such as silicone foam or silicone, or any other combination of hollow and buoyant materials, to provide buoyancy as will be known to one with skill in the art. The webbing or silicone foam does not necessarily have to be biocompatible as it will not be making direct contact with the user. As contemplated above, any suitable combination of materials may be used as will be known to one with skill in the art.

Figure 9A:
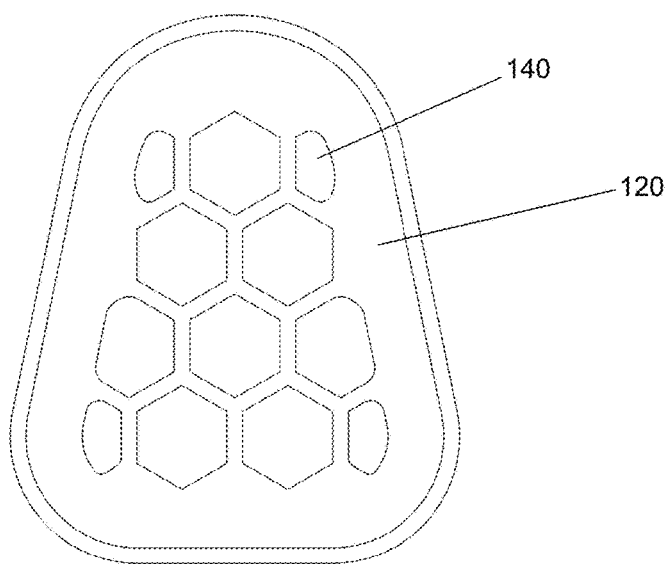
FIG. 9A is a perspective view.
Figure 9B:
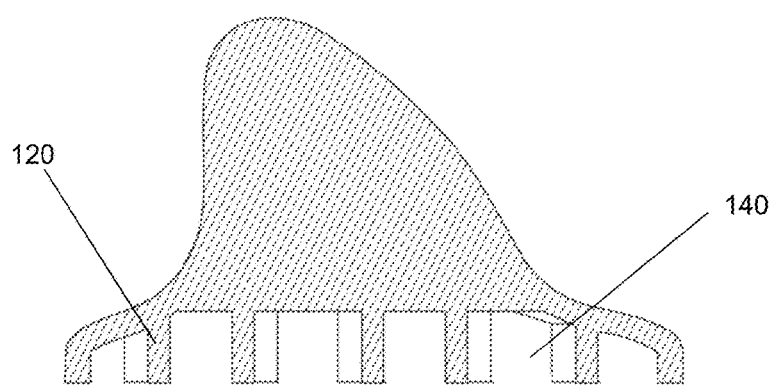
FIG. 9B is a bottom plan view of a stress urinary incontinence device comprising a honeycomb contact face in accordance with an embodiment.

In another embodiment, to increase the buoyancy of the device, the contact face 110 of the device may be modified to include one or more areas that are open, e.g. openings 140, to the inner portion 104 of the body 102. In this case, the inner portion 104 may be hollow or may include material in a webbed formation that extends to the contact face 110 of the device. For example, the contact face 110 of body 102 of the device comprises openings 140 that form a honeycomb or similar pattern, e.g. pattern of hexagons, squares, rectangles, trapezoids, etc., as shown in FIG. 9, designed to enhance the buoyancy of the device. The pattern is created such that the honeycomb or hexagons are hollow and the perimeter of the pattern is formed from a selected biocompatible material, either the same material as in the rest of the device, or a different material, that may optionally be more buoyant than the material of the rest of the device. The outer perimeter of the contact face 110, as well as the perimeter around the open shapes of the contact face, provides a surface for application of adhesive. The outer perimeter may also be increased in size to provide an enlarged surface to retain adhesive and to aid in adhesion of the device to the urethral meatus.

While the above contemplates either the body or the guide being buoyant, in still other embodiments, both of the inner portion 104 of the body 102 or the interior portion 122 of the guide 120 may be hollow or may have at least one layer of a buoyant material such as silicone foam, or combination of buoyant materials, to enable floating.

To support ease of retrieval, the device may be engineered such that the guide face 112 floats at or above the water surface to facilitate retrieval of the device from water. Thus, if the device is dropped in water, the user can readily grasp the guide 120 without submersing her hand in the water. For example, the overall density of the device is designed to be less than the water in which it is placed when the body and/or guide of the device is at least partially hollowed and/or partially filled with a buoyant material as mentioned above. The device may also be designed so that the guide is less dense than the remaining body of the device to ensure that, if immersed in water, the guide floats upwards to allow for ease of retrieval by the user. This density difference is achieved by incorporating more buoyant materials within the guide (or air from a hollow design fin) in comparison to the materials in the body of the device causing the guide to be less dense than the body as well as being less than the water into which it is inadvertently dropped or placed.

The device may be made using well-established techniques. For example, a suitably shaped mould may be filled with the material selected for use to make the device. The mould itself may be made out of nylon, aluminum or steel, or any other material suitable for making a mould for injection moulding as will be known to one with skill in the art. The mould may be heated and the material for making the device may be added under pressure to the heated mould. The heat from the mould acts to cure the material into the final product, i.e. the present device. Alternatively, the material for making the device may be heated and added under pressure to the mould.

In the case of a device comprising layers of different materials, the layers are added in the appropriate order once the previously added layer is heat cured. Hollow portions are prepared by injecting air into the material in portions of the device to include a hollow space. A two-part mold may also be utilized in which the device is prepared as 2 parts which are then combined using known techniques to form the device with hollow spaces or with different materials. Molds may also be designed to provide features such as a patterned contact face as in FIG. 9.

EXAMPLES OF USE

Other methods of manufacture can also be used as will be known to one with skill in the art.

Example 1: In use, a device, in accordance with FIG. 1 made of medical grade silicone and including a silicone hydrogel adhesive on its contact face was placed over the urethral opening beneath the inner labia and above the vaginal opening of an individual. The device was found to be effective to prevent urine leakage.

Example 2: In another example, raw silicone of an approximate size of a desired device was placed into a metal bowl that was filled with 8 inches of cold water. It was noted that solid silicone on its own is not generally buoyant. To generate a buoyant device, a plastic gum substance was wrapped around the silicone piece and a small air bubble was incorporated into the plastic gum. After immersion in the water again, the modified silicone piece was now found to be buoyant in water.

Figure 5:
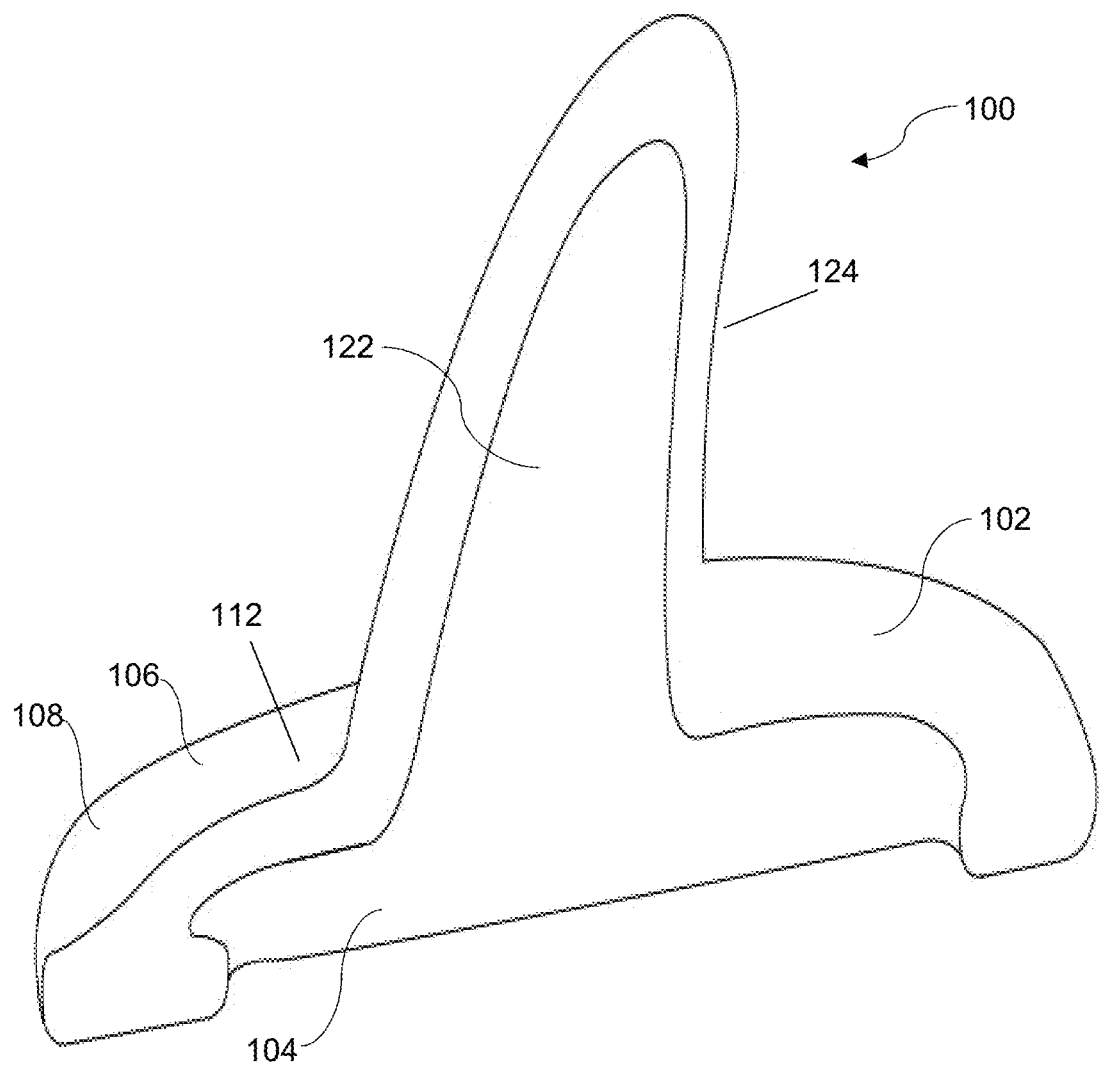
FIG. 5 shows a cutaway view of an exemplary stress urinary incontinence device having a hollow inner portion in the body and hollow interior in the guide in accordance with a further embodiment of the present invention.
Figure 6:
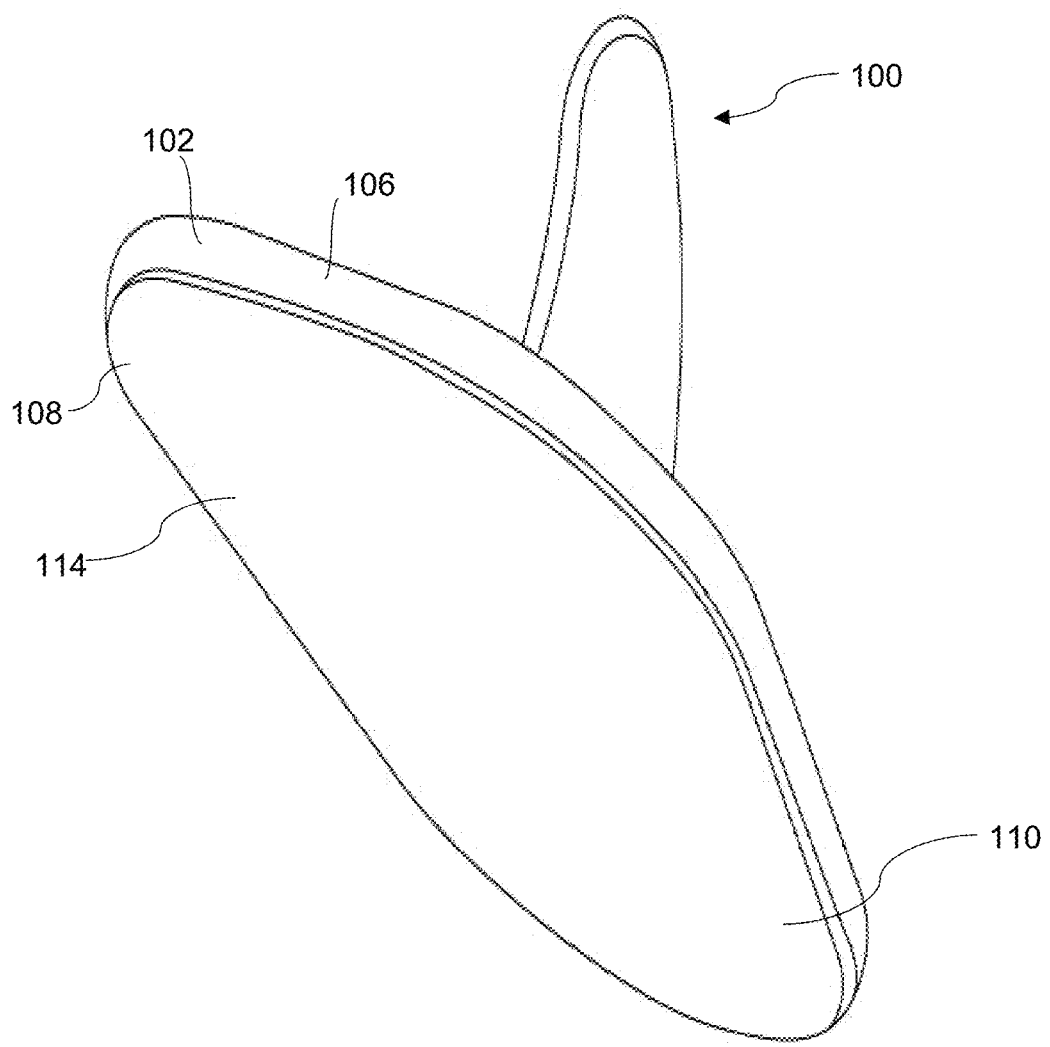
FIG. 6 shows an exemplary adhesive layer provided on a strip of an exemplary stress urinary incontinence device in accordance with a further embodiment of the present invention.

Example 3—In view of Example 2, a device was prepared of medical grade silicone comprising a hollow inner portion of the body and/or a hollow interior portion of the guide, as shown in FIG. 5. The device was found to be buoyant and effective to occlude the urethra.

Example 4—In one example, a double-sided adhesive strip was provided, with one side configured for adhesion to the contact face of the device and the opposite side configured for adhesion to the urethral meatus. Testing was conducted under various environmental conditions for over 60 medical grade adhesives over the course of an 18-month period.

To identify adhesive selection for the device, approximately 60 medical grade adhesives were tested to determine how the product fared under certain environmental conditions.

At-Home Stability Testing: Each adhesive was tested under hot and cold conditions varying between 0° C. to approximately 29° C. to determine whether or not the end use of the product would be compromised.

Adhesion Testing: A 30-person user study was conducted using prototype devices that were configured for one-time use to determine the adhesive that enabled safe application and reusability of the device. Specifically, the study tested: (1) the extent to which adhesive residue remained on the device on removal of the adhesive from the device to permit the device to be reused; (2) the strength of the adhesive on the contact face of the device as compared to the strength of the adhesive to the urethral meatus to ensure that the adhesive is removed with the device and does not remain on the body; and (3) the ability of the adhesive to maintain adhesion to the urethral meatus in the presence of moisture, to minimize or prevent movement of the device and permit removal without discomfort or sticking to body hair.

The testing revealed that the use of an adhesive product comprising two different adhesives laminated together promoted the above objectives. Adhesives found to provide suitable adhesion to the contact face of the device were acrylic and silicone based adhesives, e.g. Avery Dennison MED 6001SI soft silicone adhesive in 0.34 mm thickness. A thin double-coated trilaminate Thermoplastic Polyurethane (TPU) film was also found to be appropriate for use. The adhesive suitable for application to the urethral meatus was a medical grade hydrogel, e.g. a high tack 1.3 mil hydrogel with a pH of 3.5(+/−0.5) and water activity (aw) of 0.66 (specifically Axelgaard's AG2550 in mil thickness with a pH of 3.5) was found to be appropriate for use.

One or more currently preferred embodiments have been described by way of example. It will be apparent to persons skilled in the art that a number of variations and modifications can be made without departing from the scope of the invention as defined in the claims.

Parts List
100 incontinence device
102 body
104 inner portion
106 outer portion
108 at least one layer of biocompatible material
110 contact face
112 guide face
114 adhesive layer
120 guide
122 interior portion
124 exterior portion
130 at least one layer of silicone foam
140 openings

What is claimed is:

1. A female stress urinary incontinence device to limit or prevent leakage of urine in an individual, said device comprising:
a body comprising an inner portion surrounded by an outer portion, wherein said outer portion comprises a biocompatible material,
said outer portion of the body comprising a contact face opposing a guide face, wherein said contact face comprises a size and a shape configured to occlude the urethral opening of the individual; and
a guide projecting from the guide face to aid in application of the device onto the urethral meatus beneath the inner labia and above the vaginal opening, said guide having an interior portion surrounded by an exterior portion,
wherein the contact face of the body comprises multiple hollow openings in a webbed formation formed in the contact face that extend into the inner portion of the body; and
wherein the device is buoyant in water and reusable.

2. The device of claim 1, wherein the body comprises medical grade silicone.

3. The device of claim 1, wherein the inner portion of the body comprises silicone foam.

4. The device of claim 1, wherein the inner portion of the body is at least partially hollow.

5. The device of claim 1, wherein the interior portion of the guide is at least partially hollow.

6. The device of claim 1, wherein the interior portion of the guide comprises silicone foam.

7. The device of claim 1, wherein the guide is more buoyant in water than the body.

8. The device of claim 1, wherein the contact face of the body comprises an adhesive layer suitable to adhere to the urethral meatus.

9. The device of claim 8, wherein the adhesive is a medical grade, non-water gradient adhesive.

10. The device of claim 1, wherein the adhesive is a medical grade hydrogel.

11. The device of claim 1, wherein the guide is a triangular, round or oval fin, a ring or a knob.

12. The device of claim 1, wherein the guide and the body are integral.

13. The device of claim 1, wherein the guide is removable from the body.

14. The device of claim 1, wherein the body is comprised of varying shores of silicone with a decreasing gradient of silicone from the inner portion to the outer portion of the body.

15. The device of claim 1, wherein the body of the device has a perimeter and the body decreases in thickness towards the perimeter.

16. The device of claim 1, wherein the body is curved.

17. The device of claim 1, wherein the multiple hollow openings in the contact face comprises a honeycomb pattern that extends into the inner portion of the body.

18. A kit comprising:
i) the a device as defined in claim 1; and
ii) an adhesive for application to the contact face of the device.

19. A method comprising applying the device as defined in claim 1 to the urethral meatus of the individual to occlude the urethral opening and limit or prevent urine leakage from the urethra.

* * * * *